United States Patent [19]
Salata, Jr.

[11] Patent Number: 5,929,071
[45] Date of Patent: Jul. 27, 1999

[54] METHOD FOR THE TREATMENT OF PRETERM LABOR

[75] Inventor: Joseph J. Salata, Jr., Lansdale, Pa.

[73] Assignee: Merck & Co., Inc., Rahway, N.J.

[21] Appl. No.: 08/884,888

[22] Filed: Jun. 30, 1997

Related U.S. Application Data

[60] Provisional application No. 60/021,138, Jul. 2, 1996.

[51] Int. Cl.$^6$ ............... A01N 43/62; C07D 243/12; C07D 243/18; C07D 243/24
[52] U.S. Cl. ............... 514/221; 514/821; 510/504; 510/506; 510/509
[58] Field of Search ............... 514/221, 821; 540/504, 509, 506

[56] References Cited

U.S. PATENT DOCUMENTS

| | | | |
|---|---|---|---|
| 4,628,084 | 12/1986 | Bock et al. | 540/509 |
| 4,663,321 | 5/1987 | Bock et al. | 514/220 |
| 4,820,834 | 4/1989 | Evans et al. | 540/504 |
| 4,970,207 | 11/1990 | Sato et al. | 514/211 |
| 5,175,159 | 12/1992 | Bock et al. | 514/221 |
| 5,220,017 | 6/1993 | Bock et al. | 540/509 |
| 5,302,591 | 4/1994 | Fletcher et al. | 514/221 |
| 5,324,483 | 6/1994 | Cody et al. | 422/131 |
| 5,324,726 | 6/1994 | Bock et al. | 514/221 |
| 5,360,802 | 11/1994 | Chambers et al. | 514/221 |
| 5,426,185 | 6/1995 | Baldwin et al. | 540/509 |
| 5,428,031 | 6/1995 | Sanguinetti et al. | 514/221 |
| 5,438,055 | 8/1995 | Baldwin et al. | 514/221 |
| 5,521,175 | 5/1996 | Pineiro et al. | 514/221 |
| 5,550,126 | 8/1996 | Horwell et al. | 514/237.5 |
| 5,556,969 | 9/1996 | Chambers et al. | 540/509 |
| 5,618,812 | 4/1997 | Pineiro et al. | 514/221 |
| 5,633,251 | 5/1997 | Claremon et al. | 514/221 |

FOREIGN PATENT DOCUMENTS

| | | |
|---|---|---|
| 0 434 360 | 6/1991 | European Pat. Off. . |
| 0 434 369 | 6/1991 | European Pat. Off. . |
| 0 538 945 A1 | 4/1993 | European Pat. Off. . |
| 0 539 170 A1 | 4/1993 | European Pat. Off. . |
| WO 92/01683 | 2/1992 | WIPO . |
| WO 95/32191 | 11/1995 | WIPO . |
| WO 96/05827 | 2/1996 | WIPO . |
| WO 96/11689 | 4/1996 | WIPO . |

OTHER PUBLICATIONS

Proc. Natl. Acad. Sci., vol. 87, pp. 2975–2979 (1990), by Folander, et al.

J. Physiol., vol. 260, pp. 315–333 (1976), by Kuriyama, et al.

Evans, B.E., et al., "Design of Nonpeptidal Ligands for a Peptide Receptor: Cholecystokinin Antagonists", J. Med. Chem., vol. 30(7), pp. 1229–1239, 1987.

Craig, D.Q.M., et al., "An Investigation into the Physico-Chemical Properties of Self–Emulsifying Systems Using Low Frequency Dielectric Spectroscopy, Surface Tension Measurements and Particle Size Analysis", Inter. J. of Measurements and Particle, vol. 96, pp. 147–155, 1993.

*Primary Examiner*—Mukund J. Shah
*Assistant Examiner*—Tamthom N. Truong
*Attorney, Agent, or Firm*—J. Antonio Garcia-Rivas; Valerie J. Camara; Mark R. Daniel

[57] ABSTRACT

The invention is directed to a method useful in the treatment of preterm labor, dysmenorrhea and for the stoppage of labor preparatory to cesarean delivery.

2 Claims, No Drawings

METHOD FOR THE TREATMENT OF PRETERM LABOR

This application claims the benefit of U.S. Provisional Application No. 60/021,138, filed Jul. 2, 1996.

FIELD OF THE INVENTION

The present invention provides for a method of treating or preventing preterm labor, stopping labor preparatory to vaginal and Cesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuro-muscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

Selective $I_{Ks}$ modulators are presented which are ideal tocolytic agents. The $I_{sK}$ or minK channel gene has been cloned from diethylstibestrol (DES)—primed uterine tissue and its expression in Xenopus occytes results in a slowly activating potassium current that resembles the $I_{Ks}$ current constituitively expressed in mammalian cardiac cells. (Boyle et al., Science 235:1221–1224, 1987; Boyle et al., Nature 330:373–375, 1987; Folander et al., Proc. Nat'l. Acad. Sci. 87:2975–2979, 1990; Sanguanetti and Jurkiewicz, J. Gen. Physiol., 96;195–215, 1990). Northern analysis demonstrates that the $I_{sK}$ gene which encodes for a sub-unit of the channel that underlies the $I_{Ks}$ current, is expressed in DES-primed uterine tissue. (Folander et al., Proc. Natl. Acad. Sci. 87:2975–2979, 1990). Uterine contraction is associated with and triggered by prolonged bursts of action potentials which occur as a result of the depolarization of smooth muscle. (Kuriyama and Suzuki., J. Physiol. (London) 260:315—et seq., 1976). Therefore, activation of $I_{sK}$, resulting in membrane hyperpolarization should prevent or inhibit the maintained depolarization and bursting of action potentials and thereby inhibit smooth muscle contraction and/or promote smooth muscle relaxation.

In the instant invention, highly selective activators or agonists of $I_{Ks}$ current or $I_{sK}$ channel have been identified and characterized. These compounds which promote opening of the $I_{sK}$ channel allow effux of positively charged potassium ions ($K^+$) ions to flow out or exit cells through the cell membrane which produces a hyperpolarization of the transmembrane voltage gradient. This hyper-polarization will prevent or inhibit contraction of excitable smooth muscle cells of the uterus which occur as a direct consequence of membrane depolarization. The inhibition of smooth muscle contraction is beneficial in the treatment of preterm labor or premature uterine contraction.

The method of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By modulating the IKs current in the uterus, selective, more efficacious treatment of dysmenorrhea will result. An additional use for the present invention is for the stoppage of labor preparatory to vaginal or Cesarean delivery.

It is, therefore, a purpose of this invention to provide a method of treatment which more effectively modulates the IKs current in disease states in animals, preferably mammals, especially in humans. It is still another purpose of this invention to provide a method of modulating the IKs current in disease states in mammals. It is also a purpose of this invention to develop a method of preventing or treating disorders of preterm labor and dysmenorrhea by modulating $I_{Ks}$ current.

It has now been found that compounds of the present invention are modulators of IKs current. When the IKs current is modulated by the compounds of the present invention, the IKs channel is activated and exerts its biologic or pharmacologic effects. This method is useful in the treatment and prevention of certain gynecological and obstetrical disorders of animals, preferably mammals and especially humans. These disorders are primarily preterm labor and dysmenorrhea. This method would also find usefulness for stoppage of labor preparatory to vaginal or Cesarean delivery.

SUMMARY OF THE INVENTION

A method of preventing preterm labor in a mammal in need thereof, comprising the step of administering to said mammal a pharmacologically effective amount of a selective modulator of IKs current is presented. Further, a method of stopping labor prior to vaginal or cesarean delivery in a mammal and treatment of dysmenorrhea in a mammal in need thereof comprising administration of a pharmacologically effective amount of a modulator of IKs current is also presented.

DETAILED DESCRIPTION OF THE INVENTION

A method of preventing preterm labor in a mammal in need thereof, comprising the step of administering to said mammal a pharmacologically effective amount of a selective modulator of IKs current is presented. Further, a method of stopping labor prior to cesarean delivery in a mammal and treatment of dysmenorrhea in a mammal in need thereof comprising administration of a pharmacologically effective amount of a modulator of IKs current is also presented.

By a "selective modulator of IKs" is meant those compounds which when studied in the test disclosed herein have an agonist effect on the IKs current to produce an increase in the efflux of potassium out of the cell and hence an increase in the outward IKs current at a given transmembrane or test voltage at concentrations 1 $\mu$M and should result in treatment which is safe and effective.

Several of the compounds used according to the present invention are known per se as antagonists of gastrin and cholecystokinin (CCK). The invention includes racemic mixtures of these compounds, the separated R and S enantiomers, and preferably, the R enantiomer.

Among the compounds included within the scope of this invention are the benzodiazepine analogs of Formula I Formula I

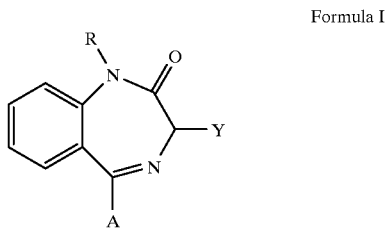

wherein
A is a 6-membered saturated or unsaturated carbocyclic ring either substituted or unsubstituted wherein the substituents may be 1 or 2 of fluoro, chloro, iodo, bromo, $C_1$–$C_6$ alkyl, either straight, branched chain or cyclic;
Y is —$NH_2$, $NHSO_2R^1$, or

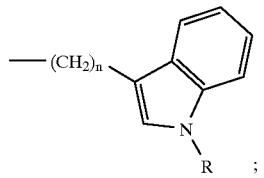

n is 0 or 1; and
R is hydrogen, straight or branched $C_{1-6}$ alkyl or $C_{1-3}$ alkylamine wherein the amino group is optionally mono- or di-substituted $C_{1-3}$ alkyl; or chloro, dichloro, methoxy, or nitroso; or a pharmaceutically acceptable salt thereof.

The most preferred example of the compounds useful in the method of treatment of this invention is 1,3-dihydro-5-(2-fluorophenyl)-3-(R)-(3'-indolyl)methyl-1-methyl-2H-1,4-benzodiazepin-2-one which has the chemical structure

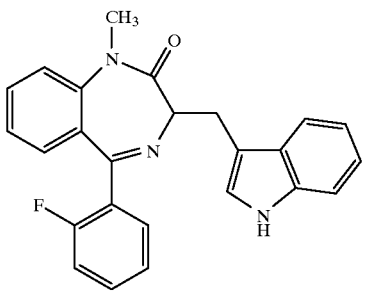

Additional example compounds are disclosed in U.S. Pat. No. 4,820,834, EP-A-0 434 360 and EP-A-0 434 369, each of which are hereby incorporated by reference. Examples of some preferred compounds are listed below of this type:

1. 3(R)-(+)-1,3-dihydro-3-(2-indolecarbonylamino)-1-methyl-5-phenyl-2H-1,4-benzodiazepin-2-one;
2. 3(S)-(−)-1,3-dihydro-3-(2-indolecarbonylamino)-1-methyl-5-phenyl-2H-1,4-benzodiazepin-2-one;
3. N-(2,3-dihydro-1-methyl-2-oxo-5-phenyl-1H-1,4-benzodiazepin-3-yl)-N'-(3-methylphenyl)urea;
4. (R)-N-(2,3-dihydro-1-methyl-2-oxo-5-phenyl-1H-1,4-benzodiazepin-3-yl)-N'-(3-methylphenyl)urea;
5. N-[3(R,S)-5-cyclohexyl-2,3-dihydro-1-methyl-2-oxo-1H-1,4-benzodiazepin-3-yl]-N'-[3-(isopropylsulfonylaminocarbonyl) phenyl]urea, example 2 herein;
6. N,N-dimethyl-4-(3(R,S)-(((3-methylphenyl)amino)-carbonyl)amino-1,3-dihydro-1-(2-methylpropyl)-2-oxo-1,4-benzodiazepin-5-yl)phenylmethylamine;
7. (R)-3-amino-1,3-dihydro-1-methyl-5-phenyl-2H-1,4-benzodiazepin-2-one;
8. N-(2,3-dihydro-1-methyl-2-oxo-5-phenyl-1H-1,4-benzodiazepin-3-yl)-N'-(m-methylphenyl)urea;
9. (±)-N-(2,3-dihydro-1-methyl-2-oxo-5-(4-pyridinyl)-1H-1,4-benzodiazepin-3-yl-1H-indole-2-carboxamide;
10. N-(2,3-dihydro-1-methyl-2-oxo-5-phenyl-1H-1,4-benzodiazepin-3-yl)-4-methylbenzenesulfonamide;
11. (R)-1-(2-(dimethylaminoethyl)-5-(2-fluorophenyl)-1,3-dihydro-3-((1-methyl-1H-indole-3-yl)methyl)-2H-benzodiazepin-2-one; and
12. N-(2,3-dihydro-1-methyl-2-oxo-5-(4-morpholino)-1H-1,4-benzodiazepin-3-yl)-N'-3-methylphenylurea; or a pharmaceutically acceptable salt thereof.

The selective modulators of IKs of the present invention have the pharmacological properties required to prevent preterm labor, stop labor prior to vaginal or Cesarean delivery and treat dysmenorrhea in a mammal in need thereof, namely they modulate the IKs current in the uterus and in so doing reduce or eliminate spasms in the uterus which result in these conditions.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The term "substituted" shall be deemed to include multiple degrees of substitution by a named substituent.

Where multiple substituent moieties are disclosed or claimed, the substituted compound can be independently substituted by one or more of the disclosed or claimed substituent moieties, singly or plurally.

The ability of the compounds of the present invention to selectively modulate IKs makes these compounds useful as pharmacologic agents for mammals, especially for humans, for the treatment and prevention of disorders wherein IKs current may be involved. Examples of such disorders include preterm labor and especially dysmenorrhea. These compounds may also find usefulness for stoppage of labor preparatory to Cesarean delivery.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.03 to about 1 mg per kg of body weight per day orally. Intravenously, the most preferred doses will range from about 0.0001 to about 10 mg per kg of body weight per day, preferably from about 0.0001 to about 2 mg per kg of body weight per day, and more preferably by intravenous delivery of from about 0.0003 to about 0.3 mg per kg of body weight per day using constant rate infusion. The dosage and rate of delivery will depend upon the response by the individual patient and the condition of the unborn child when used to prevent preterm labor or to stop or delay delivery.

Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl- methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

The activity of the compounds described herein is measured by their ability to modulate or gate the $I_{Ks}$ current while providing only limited block of the $I_{Ks}$ current as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen Physiol. 96:195–215). Myocytes are isolated by enzymatic (collagenase and protease) digestion of Langandorf perfused hearts. Single cells are then voltage clamped using 1 mm square-bore pipettes filled with 0.5 M Kgluconate, 25 mM KCl, 5 mM K(2)ATP. Cells are bathed in a solution containing, in mN: 132 NaCl, 4KCl, 1.2 MgCl$_2$, 10 HEPES, 10 glucose: pH 7.2, temp. 35° C.

Each cell is maintained at a holding potential of –50 mV. Test depolarizations are applied as voltage steps (5–7.5 s) to test potentials between −40 and +50 mV. $I_{Ks}$ is measured as time-dependent current during the pulses and as tail current upon repolarization to −50 mV. Currents are measured during control, then after exposure to drug at two different concentrations. Compounds that produce an increase in IKs current at any test potential are considered selective modulators of IKs. Compounds that produce a decrease in IKs current at any test potential are considered selective blockers of IKs.

Employing this test, the compounds described herein as selective modulators of IKs increase IKs current at concentrations 1 μM. The compounds of this invention are at least 10 times more potent in the modulation blockade of $I_{Ks}$ than of blockade of $I_{Ks}$.

EXAMPLES

Example 1

2-N-(N alpha-Boc-D-tryptophanyl)amino-2'-fluorobenzophenone

2-Amino-2'-fluorobenzophenone (4 g, 18.6 mmole), Boc-D-tryptophan (5.65 g, 18.6 mmole) and dicyclohexylcarbodiimide (DCC) (18.6 ml of a 1 M solution in methylene chloride, 18.6 mmole) were combined in 28 ml of dry tetrahydrofuran stirred in an ice bath. The mixture was allowed to warm to room temperature and stirred overnight. The solids were removed by filtration and the filtrate evaporated in vacuo. The residue was chromatographed on 9" (23 cm) of silica gel (230–400 mesh) in a 55 mm diameter column using 1 L of each of methylene chloride and 2% and 3% (v/v) diethyl ether in methylene chloride.

The product fractions were combined and evaporated in vacuo. The residue was crystallized from diethyl ether and the resulting solid dried in vacuo at 40° C. for 20 hours: (m.p. 64°–67° C.).

The compound showed a single component by thin layer chromatography (TLC) (Rf=0.36, silica gel plate eluted with 6% (v/v) diethyl ether in methylenechloride). The NMR spectrum was consistent with the title structure and verified the presence of $Et_2O$.

Anal. Calc'd for $C_{29}H_{28}FN_3O_4.Et2O$: C, 68.85; H, 6.65; N, 7.30. Found: C, 69.25; H, 6.75; N, 7.30.

Example 2

1,3-Dihydro-5-(2-fluorophenyl)-3(R)-(3'-indolyl)methyl-2H-1, 4-benzodiazeoin-2-one 2-N-(N<alpha>-Boc-D-tryptophanyl)amino-2'-fluorobenzophenone (4.0 g=8.0 mmole) in 37 ml of ethyl was stirred in an ice bath and saturated with hydrogen chloride gas for 20 minutes. The mixture was evaporated to dryness in vacuo to give 2-N-(D-tryptophanyl)amino-2'-fluorobenzophenonehydrochloride. The residue in 125 ml of methanol was treated with 30 ml of water and the pH of the mixture adjusted to 8.5–9.0 with 10% sodium hydroxide solution. The mixture was stirred at room temperature for three days.

The suspension was filtered and the resulting white solid dried in vacuo at 40° C. overnight: (m.p. 251°–254° C.).

The compound showed a single component by thin layer chromatography (TLC) (Rf=0.59, silica gel plate eluted with 1:1 (v/v) diethyl ether/methylene chloride) and by HPLC (greater than 99%). The NMR spectrum was consistent with the title structure. The mass spectrum showed a molecular ion at m/e=383.

Anal. Calcd. for $C_{24}H_{18}FN_3O$: C, 75.18; H, 4.73; N, 10.96. Found: C, 74.88; H, 4.70, N, 10.65.

Example 3

1,3-Dihydro-5-(2-fluorophenyl)-3(R)-(3'-indolyl)methyly-b 2H-1,4-benzodiazepin-2-one 2-Amino-2'-fluorobenzophenone (12.5 g=58 mmole) was stirred in 100 ml of dry tetrahydrofuran in an ice bath. D-Tryptophan acid chloride hydrochloride (16 g=62 mmole), slurried in 50 ml of tetrahydrofuran, was added over 10 minutes, and the mixture stirred 2 hours in the ice bath. The resulting solid was filtered, then added to 200 ml of methanol containing 200 ml of water. The pH was adjusted to 8.5–9.0 with 10% sodium hydroxide, the mixture was stirred for three days, then filtered. The solid was dried in vacuo at 40° C.

Example 4

1,3-Dihydro-5-(2-fluorophenyl)-3(R)-[3'-1'-methylindolyl)methyl]-1-methyl-2H-1,4-benzodiazepin-2-one (A) and 1,3-dihydro-5-(2-fluorophenyl)-3(R)-(3'-indolyl)methyl-1-methyl-2H-1,4-benzodiazepin-2-one (B)

Step A 1,3-Dihydro-5-(2-fluorophenyl)-3(R)-(3'-indolyl)methyl-2H-1,4-benzodiazepin-2-one (0.85 g, 2.2 mmole) and sodium hydride (0.11 g of a 50% suspension in mineral oil, 2.3 mmole) were stirred in 10 ml of dry, degassed dimethylformamide under nitrogen in an ice bath. After 40 minutes, methyl iodide (0 14 mL=2.25 mmole) was added in one portion. The mixture was stirred for 1.5 hours at room temperature, then poured into 100 ml of water and extracted with methylene chloride ($CH_2C_{12}$) (3×30 mL). The $CH_2C_{12}$ layers were washed with water, dried over potassium carbonate, filtered and evaporated in vacuo. The residue was chromatographed on 9" (23 cm) of silica gel (250–400 mesh) in a 55 mm diameter column eluted with 4% (v/v) diethyl ether in $CH_2C_{12}$. The first product eluted was A which was obtained as a glass upon evaporation. The solid was dried in vacuo at room temperature: (m.p. 97°–100° C.).

The compound showed a single component by thin layer chromatography (R f=0.57, silica gel plate eluted with 10% (v/v ) diethyl ether in $CH_2C_{12}$) and by HPLC (98%). The NMR spectrum was consistent with the title structure and verified the presence of $CH_2C_{12}$. The mass spectrum showed a molecular ion at m/e=411.

Anal. Calc'd. for $C_{26}H_{22}FN_3O.0.1 CH_2C_{12}$: C, 74.64; H, 5.33, N, 10.01. Found: C, 74.69; H, 5.32; N, 9.63.

Step B

The second component eluted was the monomethyl compound B which was obtained as a foam (0.66 g) upon evaporation. Crystallization from hexane/$CH_2Cl_2$ gave analytical material; (m.p. 80°–85° C.).

The compound showed a single component by thin layer chromatography (silica gel plates eluted with 4% (v/v) diethyl ether in $CH_2C_{12}$) and by HPLC (99%). The NMR spectrum was consistent with the title structure and verified the presence of $CH_2C_{12}$.

Anal. Calc'd for $C_{25}H_{20}FN_3O.0.752 CH_2C_{12}$: C, 67.06, H, 4.70; N, 9.11; Found: C, 67.04; H, 4.81; N, 9.14.

What is claimed is:

1. A method of preventing preterm labor in a mammal in need thereof, comprising the step of administering to said mammal a pharmacologically effective amount of a compound of structural Formula I:

Formula I

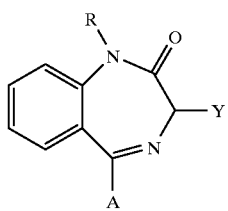

wherein

A is a 6-membered saturated or unsaturated carbocyclic ring either substituted or unsubstituted wherein the substituents may be 1 or 2 of floro, chloro, iodo, bormo, $C_1$–$C_6$ alkyl, either straight, branched chain or cyclic;

Y is

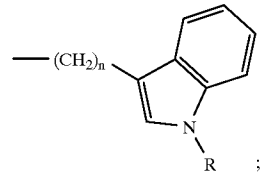

n is 0 or 1; and

R is hydrogen, straight or branched $C_{1-6}$ alkyl or $C_{1-3}$ alkylamine wherein the amino group is optionally mono- or di-substituted $C_{1-3}$ alkyl; or chloro, dichloro, methoxy, or nitroso; or a pharmaceutically acceptable salt thereof.

2. A method of preventing preterm labor in a mammal in need thereof, comprising the step of administering to said mammal a pharmacologically effective amount of 1,3-dihydro-5-(2-fluorophenyl)-3-(R)-(3'-indolyl)methyl-1-methyl-2H-1,4-benzodiazepin-2-one.

* * * * *